(12) United States Patent
Liu et al.

(10) Patent No.: US 8,815,169 B2
(45) Date of Patent: Aug. 26, 2014

(54) AIR PURIFICATION APPARATUS AND METHOD OF FORMING THE SAME

(75) Inventors: Xuanbin Liu, Shanghai (CN); Li Wang, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 514 days.

(21) Appl. No.: 12/635,523

(22) Filed: Dec. 10, 2009

(65) Prior Publication Data
US 2011/0142725 A1 Jun. 16, 2011

(51) Int. Cl.
*B01J 19/08* (2006.01)
(52) U.S. Cl.
USPC ....... 422/186.3; 422/186; 96/224; 250/423 R; 250/504 R; 250/461.1
(58) Field of Classification Search
CPC .............................. A61L 9/205; A61L 2009/14
USPC .............. 422/186.3, 186; 96/224; 250/423 R, 250/504 R, 461.1
See application file for complete search history.

(56) References Cited

U.S. PATENT DOCUMENTS

| | | | |
|---|---|---|---|
| 4,979,900 A * | 12/1990 | Okamoto et al. | 433/224 |
| 6,387,844 B1 * | 5/2002 | Fujishima et al. | 502/350 |
| 6,407,033 B1 * | 6/2002 | Kimura et al. | 502/350 |
| 6,462,947 B1 | 10/2002 | Huang | 361/695 |
| 6,730,265 B2 | 5/2004 | Horton, III | 422/24 |
| 6,761,859 B1 | 7/2004 | Oda | 422/186.3 |
| 7,255,831 B2 | 8/2007 | Wei et al. | 422/4 |
| 7,569,981 B1 * | 8/2009 | Ciancanelli | 313/300 |
| 2002/0033327 A1 * | 3/2002 | Benda et al. | 204/158.2 |
| 2002/0168305 A1 * | 11/2002 | Morrow et al. | 422/186.3 |
| 2004/0136863 A1 * | 7/2004 | Yates et al. | 422/4 |
| 2005/0020444 A1 * | 1/2005 | Hiraoka et al. | 502/350 |
| 2006/0207431 A1 * | 9/2006 | Baca et al. | 96/224 |
| 2006/0227560 A1 * | 10/2006 | Chen | 362/364 |
| 2007/0228037 A1 * | 10/2007 | Yoshiyama | 220/4.25 |
| 2007/0251812 A1 * | 11/2007 | Hayman, Jr. | 204/157.15 |
| 2008/0085224 A1 * | 4/2008 | Cheng | 422/186.3 |
| 2009/0010801 A1 | 1/2009 | Murphy et al. | 422/4 |
| 2009/0041632 A1 * | 2/2009 | Day et al. | 422/121 |

* cited by examiner

*Primary Examiner* — Xiuyu Tai
(74) *Attorney, Agent, or Firm* — Kermit D. Lopez; Luis M. Ortiz; Kevin Soules (57) ABSTRACT

A photocatalytic air purification apparatus and method of fabricating the same. The apparatus may be configured to include a light source surrounded by one or more porous plate substrates. An inner and outer surface of each plate substrate may be coated with a photocatalyst material. The light source may be placed in a direction parallel to the direction of an air flow and in optical proximity to the plate substrates in order to activate the photocatalyst coating. The photocatalyst coating associated with the plate substrates may be activated by absorbing light with a wavelength shorter than a cut-off activation wavelength from the light source in order to capture and decompose organic components and airborne pollutants in the air by the activated photocatalyst.

17 Claims, 6 Drawing Sheets

AIR PURIFICATION APPARATUS AND METHOD OF FORMING THE SAME

TECHNICAL FIELD

Embodiments are generally related to air purification. Embodiments are also related to photocatalyst materials for use in air purification. Embodiments are additionally related to photocatalytic air purification.

BACKGROUND OF THE INVENTION

Air filtration is primarily employed in commercial and residential heating, ventilation, and air cooling systems for the removal of atmospheric dust, and other undesirable airborne matter. Air filters associated with an indoor air quality (IAQ) system, for example clean the air by mechanically capturing airborne pollutants such as dust, pet hair, dander, pollen, etc, which have a relatively large size of more than 10 um. Conventional electronic air cleaners remove particles in a size range between approximately 0.3 um to 10 um. Such physical filtration approaches are limited in their effectiveness, because they do not remove smaller size contaminants such as biological contaminants and volatile organic compounds.

Photocatalysts having a strong sterilizing, deodorizing and air purifying effect have been employed in the context of air filters utilized in indoor air quality systems for air purification. One prior art approach, for example, employs an air cleaner with a photocatalyst carrying member, which is composed of a honeycomb-shaped structure. In this configuration, the photocatalyst carrying member is in contact with a lamp, which emits photons with a proper wavelength to activate a photocatalyst.

One of the problems associated with such a prior art approach stems from the fact that the limited area of the photocatalyst in the honeycomb-shaped structure is illuminated and activated by the lamp for air cleaning, which is an inefficient approach.

Another prior art technique locates a lamp to activate the photocatalyst in a direction perpendicular to the direction of air flow. A porous substrate with the light activated photocatalyst may be placed in front of the lamp. Therefore, only a portion of the light illuminating the porous substrate is employed to activate the photocatalyst and the light energy stemming from the porous substrate is typically wasted.

Based on the foregoing, it is believed that a need exists for an improved photocatalyst-based air purification apparatus and method for improving the usage efficiency of light energy employed to activate a photocatalyst, as described in greater detail herein.

BRIEF SUMMARY

The following summary is provided to facilitate an understanding of some of the innovative features unique to the present invention and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an improved air purification apparatus and method.

It is another aspect of the disclosed embodiments to provide for an improved photocatalytic air purification apparatus.

It is a further aspect of the disclosed embodiments to provide for an improved method of fabricating an air purification apparatus.

The aforementioned aspects and other objectives and advantages can now be achieved as described herein. A photocatalytic air purification apparatus and method of fabricating the same are disclosed. The apparatus can be configured to include a light source (e.g., UV lamp, fluorescence lamp, LED, etc) surrounded by one or more porous plate substrates. An inner and outer surface of each plate substrate may be coated with, for example, a photocatalyst material. The light source may be placed in a direction parallel to the direction of air flow and in optical proximity to the plate substrate(s) in order to activate the photocatalyst coating. The photocatalyst coating associated with the plate substrates may be activated by the absorption of light with a wavelength shorter than a cut-off activation wavelength from the light source in order to capture and decompose organic components in the air via the activated photocatalyst.

One or more interfacial layers can be added between the photocatalyst coating and the plate substrate to improve the adhesion between the photocatalyst and the substrate and a usage efficiency of light energy. The light source and the plate substrates can be mounted into a fixture, which is configured to include one or more buckles to fix the light source and the plates. The base of the fixture further includes a channel for a light source circuit connection.

The disclosed air purification apparatus can also be combined in a configuration that forms an array capable of being installed in and connected to an IAQ (Indoor Air Quality) system. The emission spectrum of the light source generally includes a wavelength range to activate the photocatalyst, and the plate substrate possesses a relatively high transmittance in the corresponding wavelength range of photocatalyst activation.

The spacing interval between two adjacent plate substrates can be adjusted and the substrates configured in any shape. The number of plates employed depends on the transmittance of the plate in the corresponding activation wavelength range. The light source can also be located near the periphery of an inner plate substrate. The inner and outer surface of the substrates may be configured with a porous and/or a coarse structure with dimensions on the order of microns or nanometers to improve surface area of the substrates and the coverage area of the photocatalyst, thereby improving air purification efficiency.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof.

Figure 1:
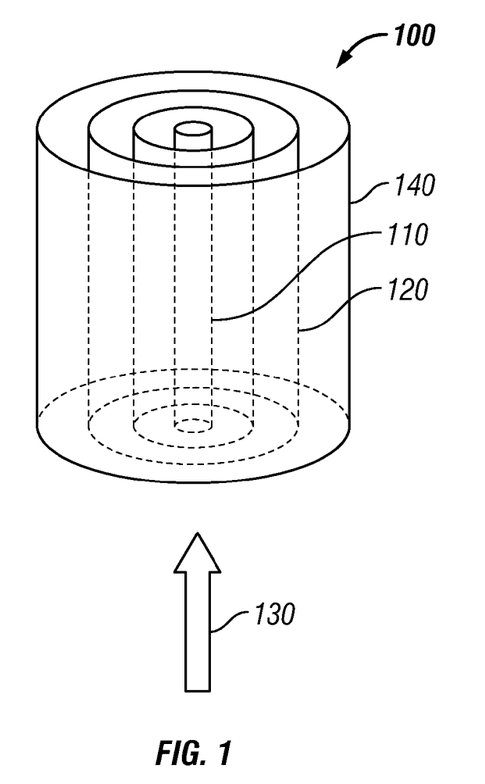
FIG. 1 illustrates a perspective view of an air purification apparatus, in accordance with the disclosed embodiments.

FIG. 1 illustrates a perspective view of an air purification apparatus 100, in accordance with the disclosed embodiments. The air purification apparatus 100 may be preferably installed in a wall of a room and located in an air passage through which the air of the room is circulated. The apparatus 100 purifies the air (e.g., treated fluid) passing through the passage. Further, the apparatus 100 can also be installed in association with an IAQ system to clean air by mechanically capturing airborne pollutants and smaller size contaminants, such as biological contaminants and volatile organic compounds.

The air purification apparatus 100 can be configured to include a light source 110 and one or more plate substrates 120. Each plate substrate 120 can be coated with a photocatalyst material 140 both on an internal surface and an exterior surface. The light source 110 can be placed in a center surrounded by the plate substrates 120. In addition, the light source 110 can be placed in a direction parallel to the direction of an air flow 130 and in optical proximity to the plate substrates 120 in order to activate the photocatalyst coating 140. The emission spectrum of the light source 110 includes a wavelength range to activate the photocatalyst coating 140.

The plate substrates 120 possess a relative high transmittance in the corresponding wavelength range of photocatalyst activation. The photocatalyst coating 140 on the internal and exterior surface of the plate substrates 120 can be activated by absorbing the light with a wavelength shorter than its cut-off activation wavelength. A variety of light sources such as, for example, ultraviolet (UV) and visible lamps can be employed to illuminate the photocatalyst coating 140. However, it will be apparent to those of skill in the art that other light sources such as fluorescence lamp, LED or the like, can be substituted if the photocatalyst material is visible light responsive. Thus, the light source 110 can, for example, can be an ultra violet lamp, a fluorescence lamp, a light emitting diode, etc.

Another example of a light source that can be utilized as light source 110 is a VCSEL (Vertical Cavity Surface Emitting Laser), which is a type of semiconductor laser diode with laser beam emission perpendicular from the top surface, contrary to conventional edge-emitting semiconductor lasers (also in-plane lasers) which emit from surfaces formed by cleaving the individual chip out of a wafer.

Figure 2:
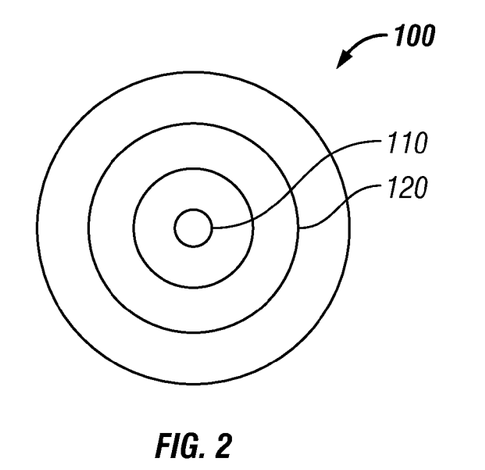
FIG. 2 illustrates a top view of the air purification apparatus depicted in FIG. 1, in accordance with the disclosed embodiments.

FIG. 2 illustrates a top view of the air purification apparatus 100, in accordance with the disclosed embodiments. Note that in FIGS. 1-11, identical or similar parts or elements are generally indicated by identical reference numerals. The light source 110 can be placed in a direction parallel to the direction of the air flow 130 so that the organic components in the air can be captured and decomposed by the activated photocatalyst coating 140. The spacing interval between two adjacent plate substrates 120 can be adjusted depending upon design considerations. The larger interval may lead to less wind resistance as the plate permits the transmittance of light in the wavelength range of photocatalyst activation and the light beam emitted from the light source 110 can be transmitted through a number of plate substrates 120.

The number of plate substrates 120 depends on the transmittance of the plate substrate 120 in the corresponding activation wavelength range. More plate can be placed for higher transmittance. The transmittance characteristics associated with the plate substrates 120 can be consistent with the emission spectrum of the light source 110 and response spectrum of the photocatalyst material 140. For example, if the light source 110 is an UV lamp with dominant wavelength of 254 nm, the plate substrate 120 also possesses a relative large transmittance, such as 20% or more, in the wavelength range around 254 nm. Higher transmittance of the plate substrate 120 in the corresponding wavelength range of photocatalyst activation allows the placement additional plate substrates, such as, for example, substrate 120, which are then capable of employing increased light energy to achieve a higher air purifying efficiency.

The plate substrates 120 described herein can be configured from a material such as, for example, quartz glass, ultra violet ray transmitting glass or polymer, borosilicate glass, sapphire, magnesium fluoride ($MgF_2$), lithium fluoride (LiF), polymethyl-methacrylate (PMMA), depending upon design considerations. The plate can be configured from material which can absorb or block ultra violet rays. The plate may also be configured from material such as, common glass, PC, PS, PET, etc if visible light responsive photocatalyst and visible light source are selected. It can be appreciated that other types of materials can be utilized in place of the suggested material.

Figure 3:
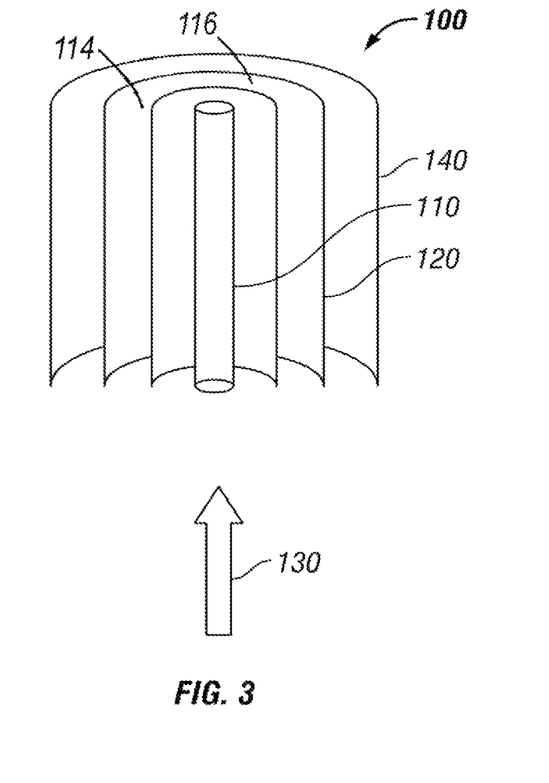
FIG. 3 illustrates a cross-sectional view of the air purification apparatus depicted in FIG. 1, in accordance with the disclosed embodiments.

FIG. 3 illustrates a cross-sectional view of the air purification apparatus 100, in accordance with the disclosed embodiments. The internal and exterior surface of each plate substrate 120 can be configured to include a porous and/or coarse structure. For example, the surface of the plate substrates 120 can be shaped such that it possesses a lot of tiny protrusions or pores. The dimension of protrusions or pores can be in the order of micron or nanometer in order to increase a specific surface area of the plate substrates 120 and a coverage area of photocatalyst coating 140 and to improve the air purifying efficiency. The porous and nontransparent material associated with the plate substrates 120 may capture organic gas molecules effectively, such as active carbon, metal foam, cordierite, sponge, etc or combination thereof. In such a case, only a few plate substrates 120 are required to surround the light source 110.

An interfacial layer 114 can be added between the photocatalyst coating 140 and the plate substrates 120 in order to improve the usage efficiency of light energy and to enhance transmittance. For example, the interfacial layer 114 such as MgF2 can be deposited on the plate substrates 120 by many different techniques such as, for example, physical vapor deposition, chemical vapor deposition (CVD), liquid phase deposition (LPD), dipping, sputtering, etc. Another interfacial layer 116 may also be added to improve the adhesion between the photocatalyst material and the plate substrates 120 and to prevent the oxidation effect of photocatalyst on the plate substrates 120. For example, the sub layer such as, SiO2 can be coated on the surface of the plate substrates 120 to improve photocatalyst adhesion, depending on the substrate and the photocatalyst material selection.

Figure 4:
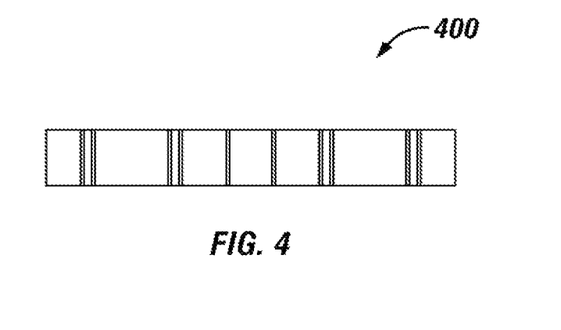
FIG. 4 illustrates a top view of a fixture associated with the air purification apparatus, in accordance with the disclosed embodiments.
Figure 5:
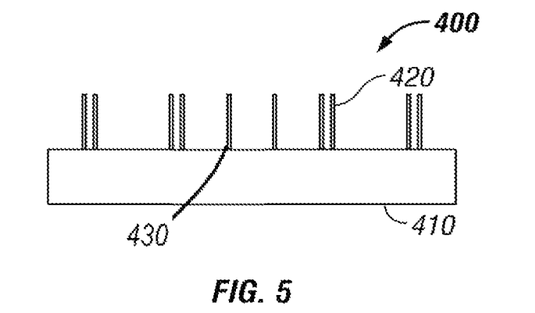
FIG. 5 illustrates a front view of the fixture associated with the air purification apparatus, in accordance with the disclosed embodiments.
Figure 6:
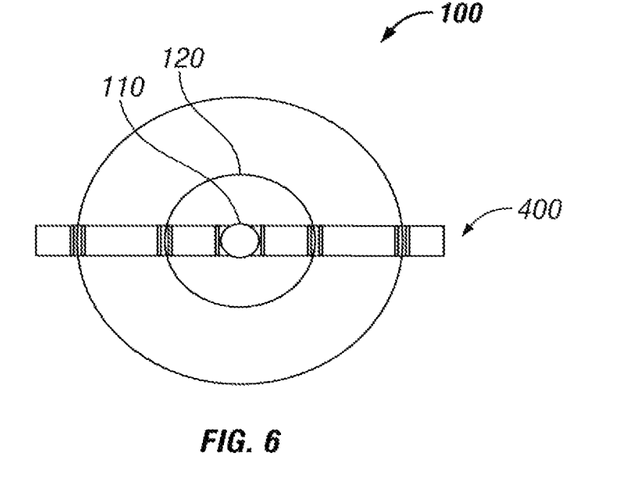
FIG. 6 illustrates a top view of the air purification apparatus mounted onto the fixture, in accordance with the disclosed embodiments.

FIG. 4 illustrates a top view of a fixture 400 associated with the air purification apparatus 100, in accordance with the disclosed embodiments, The fixture 400 generally includes a base 410 and one or more buckles 420 in order to fix the light source 110 and the plate substrates 120, as depicted in FIG. 5. FIG. 6 illustrates a top view of the air purification apparatus 100 mounted onto the fixture 400, in accordance with the disclosed embodiments. The buckles 420 can be employed to fix the light source 110 and the plate substrates 120. The base 410 associated with the fixture 400 possess channels 430 for circuit connection with respect to the light source 110.

Figure 7:
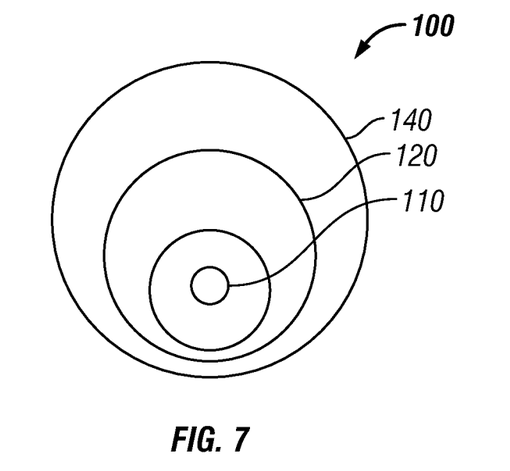
FIG. 7 illustrates a top view of the air purification apparatus associated with a light source placed near the periphery of an inner plate substrate, in accordance with the disclosed embodiments.

The photocatalyst described herein can be configured from a material such as, for example, $TiO_2$, ZnO, $Fe_2O_3$, CdS, CdSe, $WO_3$, $MoO_3$, $V_2O_5$, $SnO_2$, depending upon design considerations. For example, the spectral response of $TiO_2$ can be extended to a visible light range by doping elements such as, Fe, Cr, Co, Mo, V, B, C, N, S and F in order to modify $TiO_2$. The size of the photocatalyst particle can be in nm range (e.g., approximately 20 nm or less for $TiO_2$ related particles) for high photocatalytic activity. It can be appreciated that other types of materials can be utilized in place of the suggested material. FIG. 7 illustrates a top view of the air purification apparatus 100, in accordance with the disclosed embodiments. The light source 110 can be placed near the periphery of the inner plate substrate 120 as long as the light source 110 can be surrounded by the plate substrates 120.

Figure 8:
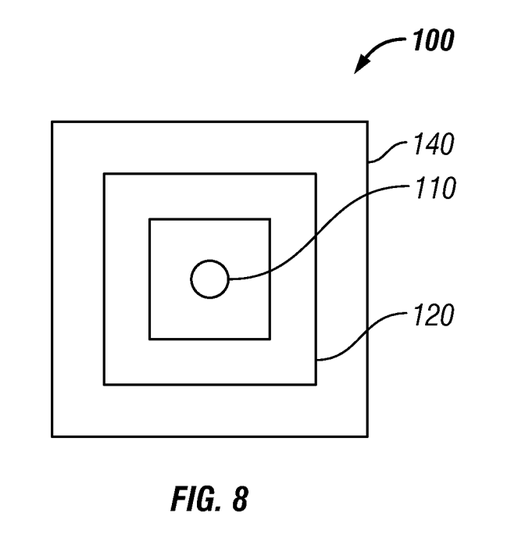
FIG. 8 illustrates a top view of the air purification apparatus associated with a rectangular plate substrate, in accordance with the disclosed embodiments.
Figure 9:
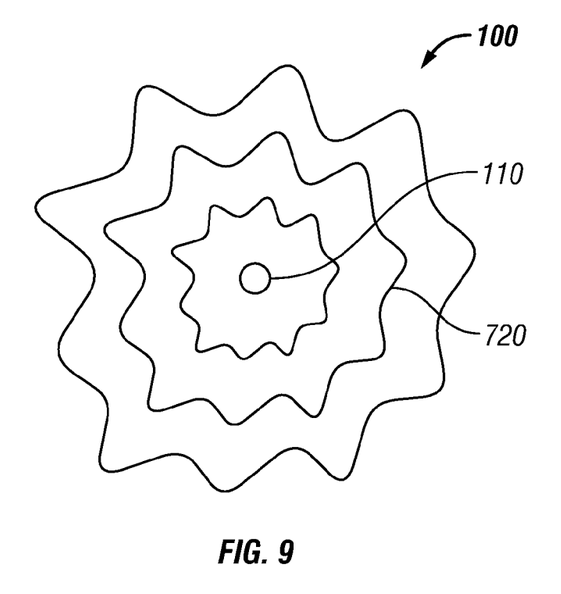
FIG. 9 illustrates a top view of the air purification apparatus associated with a corrugated plate substrate, in accordance with the disclosed embodiments.

FIG. 8 illustrates a top view of the air purification apparatus 100 associated with rectangular shape plate substrates 620 surrounding the light source 110. Again, as a reminder, in FIGS. 1-11, identical or similar elements and components are generally indicated by identical reference numerals. FIG. 9 illustrates a top view of an air purification apparatus 100 associated with an arbitrary shape plate substrates 720 surrounding the light source 110, in accordance with the disclosed embodiments. The plate substrates 120 may also be shaped in wavy or corrugated shape, honeycomb-shape, depending upon design considerations. These shapes are described for purposes of clarity and specificity; however, they should not be interpreted as limiting features of the disclosed invention. Other shapes are possible. It will be apparent, however, to those of skill in the art that such shapes can be altered without departing from the scope of the invention.

Figure 10:
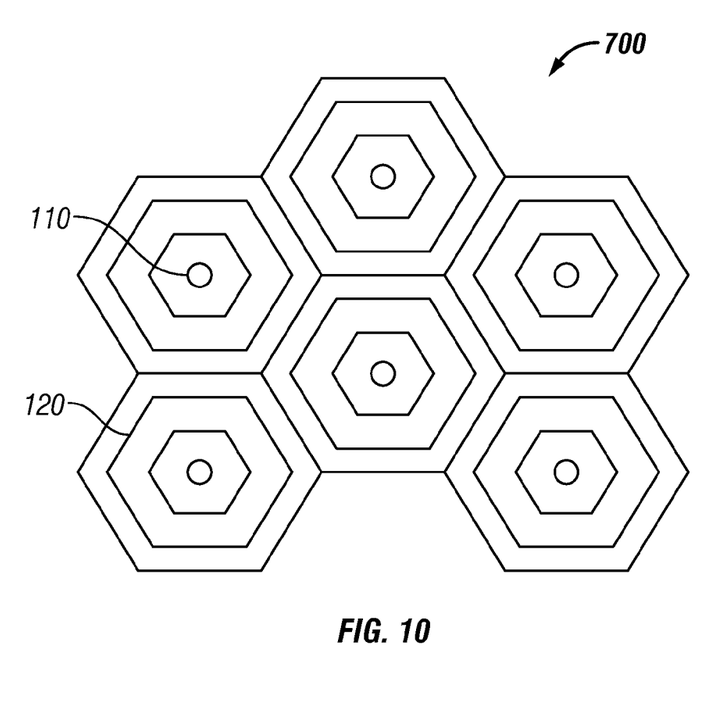
FIG. 10 illustrates a top view of an array of air purification apparatus, in accordance with the disclosed embodiments.

FIG. 10 illustrates a top view of an array of air purification apparatus 700, in accordance with the disclosed embodiments. One or more air purification apparatus 100 can be combined to form the air purification cell array 700. The photocatalyst coating 140 can be prepared by coating the photocatalyst on both sides of each porous substrate plate 120. The air purification apparatus 100 oxidize volatile organic compounds or other unwanted, toxic or combustible vapors using the photocatalyst coating 140.

Figure 11:
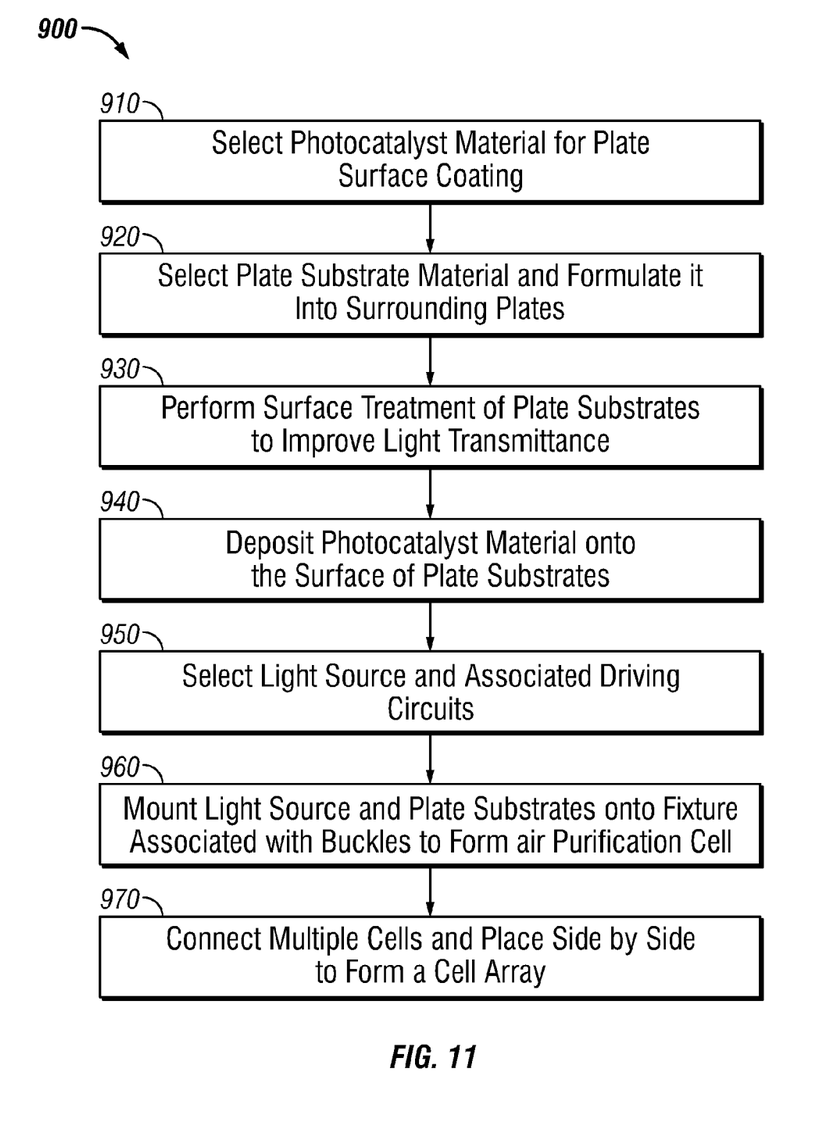
FIG. 11 illustrates a high-level flow chart of operations illustrating logical operational steps of a method for fabricating the air purification apparatus, in accordance with the disclosed embodiments.

FIG. 11 illustrates a high-level flow chart of operations illustrating logical operational steps of a method 900 for fabricating the air purification apparatus 100, in accordance with the disclosed embodiments. The photocatalyst material can be selected for coating the surface of the plate substrate 120 (and/or additional substrates) as illustrated at block 910. The substrate material can be selected and formulated into the surrounding plate substrates 120, as illustrated at block 920. The surface treatment of the plate substrates 120 can be performed to improve light transmittance, as indicated at block 930. The surface treatment of the plate substrates 120 may include the process of coating the interfacial layer and another sub-layer to improve photocatalyst adhesion and prevent the oxidation effect of the photocatalyst on the substrate 120.

Thereafter, the photocatalyst material can be then deposited onto the surface of plate substrates 120, as depicted at block 940. The photocatalyst material can be in the form of powder or a thin film on the surface of plate substrates 120. For $TiO_2$ photocatalyst, the deposition process includes sol-gel, LPD, CVD, thermal decomposition, magnetron sputtering, etc. For example, with $TiO_2$ water solution, the plate substrate 120 can be placed into a solution first, and then taken out after some time followed by natural dry at room temperature or dry at proper temperature in some heating device, such as oven, or dry near some heating source. Consequently, the internal and exterior surfaces of the plate substrates 120 can be coated with the photocatalyst particles. It can be appreciated, of course, that other types of coating methods such as, spraying the photocatalyst solution with an ejection gun can be utilized to deposit the photocatalyst onto the surface of plate substrates 120. In such a case, for better coating effect, the nozzle diameter of the ejection gun can be desired to be less than 0.5 mm.

The light source 110 and the associated driving circuits can be selected, as depicted at block 950. Thereafter, as indicated at block 960, the light source 110 and the plate substrates 120 can be mounted onto the fixture 400 to form the air purification apparatus 100. The air purification cells can then be combined in order to form the air purification cell array 700 comprising a number of air purification cells connected and placed side by side, as illustrated at block 970. It is believed that by utilizing the apparatus and approach described herein, air purifying efficiency can be improved to a considerable extent. The air purification apparatus 100 described herein can be adapted to increase the illumination area of the photocatalyst coating 140 to a considerable extent and improves usage efficiency of light energy employed to activate the photocatalyst.

Based on the foregoing, it can be appreciated that in an embodiment, an air purification apparatus can include one or more plate substrates, wherein each substrate is configured with an inner surface and an outer surface. In such an embodiment, the inner and outer surfaces can be coated with a photocatalyst such that the plate substrate (or substrates) possesses a relatively high transmittance with respect to a wavelength range for activating the photocatalyst. An embodiment of such an apparatus can further include a light source surrounded by the plate substrate(s) and located in a direction parallel to a direction of air flow. The plate substrate(s) can absorb light energy with a wavelength shorter than a "cut-off" activation wavelength to activate the photocatalyst and thereby improve the usage efficiency of the light energy and the air purification efficiency for purification of air by the air purification apparatus. The photocatalyst, when activated, can capture and decompose organic components and airborne pollutants in the air.

In another embodiment of the disclosed air purification apparatus, an interfacial layer can be coated between the plate substrate(s) and the photocatalyst in order to improve photocatalyst adhesion and to prevent oxidation of the photocatalyst with respect to the plate substrate(s). In still a further embodiment, the air purification apparatus can include a fixture associated with a plurality of fixture buckles for mounting the plate substrate(s) and the light source. Additionally, a channel can be formed/configured from and located at a base of the fixture to provide an electrical circuit connection to the light source. Additionally, a cell array can be provided, which includes a plurality of air purification cells mounted on the fixture for decomposing airborne pollutants.

In still another embodiment of the disclosed air purification apparatus, the plate substrate(s) can be configured to include, for example, a porous structure configured on the inner surface and the outer surface of the plate substrate(s) to increase a surface area with respect to the plate substrate(s) and a coverage area with respect to the photocatalyst. Alternatively, the plate substrate(s) can be configured to include a coarse structure configured on the inner surface and the outer surface of the plate substrate(s) to increase a surface area with respect to the plate substrate(s) and a coverage area with respect to the photocatalyst. The disclosed light source can be configured from a number of appropriate light sources. For example, the disclosed light source can be an ultra violet lamp, a fluorescence lamp, a light emitting diode, a VCSEL, and so forth. In some embodiments of the disclosed air purification apparatus, the plate substrate(s) can be configured from materials, such as, but not limited to quartz glass; ultra-violet ray transmitting glass; a polymer; borosilicate glass; sapphire; magnesium fluoride; lithium fluoride; a polymethyl-methacrylate; and/or a plastic sheet material. The disclosed photocatalyst can be configured from, for example, materials such as, but not limited to $TiO_2$, $ZnO$, $Fe_2O_3$, $CdS$, $CdSe$, $WO_3$, $MoO_3$, $V_2O_5$, and $SnO_2$. The disclosed interfacial layer can be configured from, for example, magnesium fluoride, silicon dioxide and so forth.

In some embodiments of the disclosed air purification apparatus, the photocatalyst and the interfacial layer can be coated on the plate substrate(s) via a process such as, but not limited to physical vapor deposition, chemical vapor deposition, liquid phase deposition, dipping, and sputtering. In varying embodiments of the disclosed air purification apparatus, the plate substrate(s) can have a shape such as, for example, a round shape, a rectangular shape, an arbitrary shape, a honeycomb shape, or another appropriate shape.

It can be further appreciated that embodiments are disclosed which relate to a method of configuring the disclosed air purification apparatus. Such a method can include, for example, configuring one or more plate substrates to include an inner surface and an outer surface, coating the inner and outer surfaces with a photocatalyst to ensure that the plate substrate(s) possesses a relatively high transmittance with respect to a wavelength range for activating the photocatalyst, and surrounding a light source by the plate substrate in a direction parallel to a direction of air flow, wherein the plate substrate(s) absorbs a light energy with a wavelength shorter than a cut-off activation wavelength to activate the photocatalyst and thereby improve a usage efficiency of the light energy and an air purification efficiency for purification of air by the apparatus. Additionally, in such a method, the photocatalyst, when activated, can capture and decompose organic components and airborne pollutants in the air.

In some embodiments of the disclosed method, a processing step can be performed for coating an interfacial layer between the plate substrate(s) and the photocatalyst in order to a photocatalyst adhesion thereof and to prevent oxidation of the photocatalyst with respect to the plate substrate(s). In still other embodiments of such a method, a fixture can be associated with a plurality of fixture buckles for mounting the plate substrate(s) and the light source. A channel can then be configured from and located at the base of the fixture to provide an electrical circuit connection to the light source. A cell array can then be formed, which includes a cell array that includes a plurality of air purification cells mounted on the fixture for decomposing airborne pollutants.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An air purification apparatus, comprising:
   a plurality of plate substrates each having an inner surface and an outer surface, wherein said inner and outer surfaces are coated with a photocatalyst and wherein said plurality of plate substrates possess a relatively high transmittance with respect to a wavelength range for activating said photocatalyst wherein a total number of said plurality of plate substrates is dependent on said transmittance;
   an adjustable interval between each of said plurality adjacent plate substrates;
   a light source surrounded by said plurality of plate substrates and located in a direction parallel to a direction of air flow, wherein said plurality of plate substrates absorbs a light energy with a wavelength shorter than a cut-off activation wavelength to activate said photocatalyst and thereby improve a usage efficiency of said light energy and an air purification efficiency for purification of air by said apparatus;
   a fixture associated with a plurality of fixture buckle for mounting said plurality of plate substrates and said light source; and
   a channel formed from and located at a base of said fixture providing an electrical circuit connection to said light source.

2. The apparatus of claim 1 further comprising arranging said light source near a periphery of an inner most of said plurality of plate substrates wherein said photocatalyst, when activated, captures and decomposes organic components and airborne pollutants in said air.

3. The apparatus of claim 1 further comprising:
   a plurality of interfacial layers coated between said plurality of plate substrates and said photocatalyst wherein at least one of said plurality of interfacial layers is configured to improve a usage efficiency of light energy, wherein at least another of said plurality of interfacial layers is configured to improve a photocatalyst adhesion and to prevent oxidation of said photocatalyst with respect to said plurality of plate substrates.

4. The apparatus of claim 1 further comprising a cell array comprising a plurality of air purification cells mounted on said fixtures for decomposing airborne pollutants.

5. The apparatus of claim 1 wherein said plurality of plate substrates further comprises:
   a porous structure to increase a surface area with respect to said plurality of plate substrates and a coverage area with respect to said photocatalyst.

6. The apparatus of claim 1 wherein said plurality of plate substrates further comprises:
   a coarse structure to increase a surface area with respect to said plurality of plate substrates and a coverage area with respect to said photocatalyst.

7. The apparatus of claim 1 wherein said light source is configured to be a VCSEL.

8. The apparatus of claim 1 wherein said plurality of plate substrates are configured from at least one of the following types of materials:
- ultra-violet ray transmitting glass;
- sapphire;
- magnesium fluoride;
- lithium fluoride; and
- a polymethyl-methacrylate.

9. The apparatus of claim 1 wherein said photocatalyst is configured from at least one of the following types of materials:
- $Fe_2O_3$, $CdSe$, $WO_3$, $MoO_3$, and $V_2O_5$.

10. The apparatus of claim 3 wherein at least another of said plurality of interfacial layers is configured from magnesium fluoride and is configured to enhance transmittance.

11. The apparatus of claim 10 wherein said photocatalyst and said interfacial layer is coated on said plurality of plate substrates via a process selected from a group of processes comprising at least one of the following: physical vapor deposition, chemical vapor deposition, liquid phase deposition, dipping, and sputtering.

12. The apparatus of claim 2 wherein said plurality of plate substrates are configured to comprise at least one of the following types of shapes: a rectangular shape, a corrugated shape, and a honeycomb shape.

13. An air purification apparatus, comprising:
- a plurality of plate substrates each having an inner surface and an outer surface, wherein said inner and outer surfaces are coated with a photocatalyst and wherein said plurality of plate substrates possesses a relatively high transmittance with respect to a wavelength range for activating said photocatalyst wherein a total number of said plurality of plate substrates is dependent on said transmittance;
- an adjustable interval between each of said plurality adjacent plate substrates;
- a light source surrounded by said plurality of plate substrates and located in a direction parallel to a direction of air flow, wherein said plurality of plate substrates absorbs a light energy with a wavelength shorter than a cut-off activation wavelength to activate said photocatalyst and thereby improve a usage efficiency of said light energy and an air purification efficiency for purification of air by said apparatus;
- a plurality of interfacial layers coated between said plurality of plate substrates and said photocatalyst wherein at least one of said plurality of interfacial layers is configured to improve a usage efficiency of light energy, wherein at least another of said plurality of interfacial layers is configured to improve a photocatalyst adhesion and to prevent oxidation of said photocatalyst with respect to said plurality of plate substrates, wherein said photocatalyst, when activated, captures and decomposes organic components and airborne pollutants in said air;
- a fixture associated with a plurality of fixture buckle for mounting said plurality of plate substrates and said light source;
- a channel formed from and located at a base of said fixture providing an electrical circuit connection to said light source; and
- a cell array comprising a plurality of air purification cells mounted on said fixture for decomposing airborne pollutants.

14. The apparatus of claim 13 wherein said plurality of plate substrates is configured to comprise at least one of the following types of shapes: a rectangular shape, a corrugated shape, and a honeycomb shape.

15. A method of configuring an air purification apparatus, said method comprising:
- configuring a plurality of plate substrates to include an inner surface and an outer surface,
- coating said inner and outer surfaces with a photocatalyst to ensure that said plurality of plate substrates possess a relatively high transmittance with respect to a wavelength range for activating said photocatalyst wherein a total number of said plurality of plate substrates is dependent on said transmittance;
- adjusting an interval between each of said plurality of adjacent plate substrates;
- surrounding a light source by said plurality of plate substrates and located in a direction parallel to a direction of air flow, wherein said plurality of plate substrates absorb a light energy with a wavelength shorter than a cut-off activation wavelength to activate said photocatalyst and thereby improve a usage efficiency of said light energy and an air purification efficiency for purification of air by said apparatus;
- associating a fixture with a plurality of fixture buckle for mounting said plurality of plate substrates and said light source;
- configuring a channel formed from and located at a base of said fixture providing an electrical circuit connection to said light source; and
- forming a cell array that includes a plurality of air purification cells mounted on said fixture for decomposing airborne pollutants.

16. The method of claim 15 further comprising arranging said light source near a periphery of an inner most of said plurality of plate substrates wherein said photocatalyst, when activated, captures and decomposes organic components and airborne pollutants in said air.

17. The method of claim 15 further comprising:
- coating a plurality of interfacial layers between said plurality of plate substrates and said photocatalyst wherein at least one of said plurality of interfacial layers is configured to improve a usage efficiency of light energy and enhance transmittance, wherein at least another of said plurality of interfacial layers is configured to improve a photocatalyst adhesion thereof and to prevent oxidation of said photocatalyst with respect to said plurality of plate substrates.

* * * * *